United States Patent
Wang et al.

(10) Patent No.: US 6,893,552 B1
(45) Date of Patent: May 17, 2005

(54) MICROSENSORS FOR GLUCOSE AND INSULIN MONITORING

(75) Inventors: Joseph Wang, Las Cruces, NM (US); Xueji Zhang, Sarasota, FL (US); Fang Lu, Millbrae, CA (US)

(73) Assignee: Arrowhead Center, Inc., Las Cruces, NM (US)

( * ) Notice: Subject to any disclaimer, the term of this patent is extended or adjusted under 35 U.S.C. 154(b) by 538 days.

(21) Appl. No.: 10/046,032

(22) Filed: Oct. 23, 2001

Related U.S. Application Data

(63) Continuation-in-part of application No. 09/216,353, filed on Dec. 18, 1998, now abandoned.
(60) Provisional application No. 60/267,811, filed on Feb. 8, 2001, and provisional application No. 60/068,916, filed on Dec. 29, 1997.

(51) Int. Cl.[7] ............................................. G01N 27/327
(52) U.S. Cl. ........................... 205/777.5; 204/403.14; 204/403.11
(58) Field of Search .................. 204/403.1, 403.11, 204/403.14; 205/777.5

(56) References Cited

U.S. PATENT DOCUMENTS

| | | |
|---|---|---|
| 3,019,383 A | 1/1962 | Varian |
| 3,837,339 A | 9/1974 | Aisenberg et al. |
| 4,220,503 A | 9/1980 | Johnson |
| 4,317,879 A | 3/1982 | Busby et al. |
| 4,350,955 A | 9/1982 | Jackson et al. |
| 4,356,074 A | 10/1982 | Johnson |
| 4,484,987 A | 11/1984 | Gough |
| 4,587,100 A | 5/1986 | Amano et al. |
| 4,604,182 A | 8/1986 | Seago |
| 4,671,288 A | 6/1987 | Gough |
| 4,704,029 A | 11/1987 | Van Heuvelen |
| 4,721,677 A | 1/1988 | Clark, Jr. |
| 4,936,956 A | 6/1990 | Wrighton |
| 4,970,145 A | 11/1990 | Bennetto et al. |
| 5,071,537 A * | 12/1991 | Yamaguchi et al. ........ 204/414 |
| 5,082,550 A | 1/1992 | Rishpon et al. |
| 5,227,042 A | 7/1993 | Zawodzinski et al. |
| 5,272,087 A | 12/1993 | El Murr et al. |
| 5,286,364 A | 2/1994 | Yacynych et al. |
| 5,330,634 A * | 7/1994 | Wong et al. ............. 205/777.5 |
| 5,378,628 A | 1/1995 | Gratzel et al. |
| 5,405,766 A | 4/1995 | Kallury et al. |
| 5,429,726 A | 7/1995 | Johnson et al. |
| 5,531,878 A | 7/1996 | Vadgama et al. |
| 5,540,828 A | 7/1996 | Yacynych |
| 5,616,222 A | 4/1997 | Maley et al. |
| 5,643,721 A | 7/1997 | Spring et al. |
| 5,708,247 A | 1/1998 | McAleer et al. |

(Continued)

FOREIGN PATENT DOCUMENTS

| | | | |
|---|---|---|---|
| EP | 0 401 179 A1 | 12/1990 | |
| JP | 04326054 A | 4/1991 | |
| JP | 09-94231 A * | 4/1997 | ............ A61B/5/00 |
| WO | WO96/14026 A1 | 5/1996 | |
| WO | WO01/20019 A2 | 3/2001 | |

OTHER PUBLICATIONS

JPO computer translation of JP 09–94231 A (Ikariyama et al.).*

(Continued)

*Primary Examiner*—Alex Noguerola
(74) *Attorney, Agent, or Firm*—Peacock Myers & Adams PC; Stephen A. Slusher

(57) ABSTRACT

A dual sensor for the simultaneous amperometric monitoring of glucose and insulin, wherein the glucose probe is based on the biocatalytic action of glucose oxidase, and the insulin probe is based on the electrocatalytic activity of metal oxide. Further provided is an oxidase enzyme composite electrode with an internal oxygen-rich binder. The present invention also optionally includes metallizing components within the carbon paste to eliminate signals from interfering compounds. The present invention includes embodiments for both in vitro and in vivo uses.

46 Claims, 11 Drawing Sheets

U.S. PATENT DOCUMENTS

| | | | | |
|---|---|---|---|---|
| 5,711,861 A | * | 1/1998 | Ward et al. | 600/347 |
| 5,771,891 A | | 6/1998 | Gozani | |
| 5,820,622 A | | 10/1998 | Gross et al. | |
| 5,922,183 A | | 7/1999 | Rauh | |
| 6,134,461 A | | 10/2000 | Say et al. | |

OTHER PUBLICATIONS

Parellada et al. ("A new tyupe of hydrophilic carbon paste electrodes for biosensor manufacturing: binder paste electrodes," Biosensors & Bioelectronics vol. 12 No. 4, pp. 267–275, Jun. 11, 1997).*

Cass, A.E.G., et al., "Ferrocene–Mediated Enzyme Electrode for Amperometric Determine of Glucose," *Anal. Chem*, vol. 56, No. 4 pp 667–671 (Apr. 1984).

Clark, Jr. L.C., "Bioelectrodes for Tissue Metabolism," *Ann NU Acad Sci.*, vol. 148, pp 133–135 (1962).

Clark, et al., "Survival of Mammals Breathing Organic Liquids Equilibrated with Oxygen at Atmospheric Pressure," *Science*, vol. 1552, PP 1755 (1966) Abstract Only.

Csoregi, E., et al., "Design, Characterization , and One–Point in Vivo Calibration of a Subcutaneously Implanted Glucose Electrode," *Anal. Chem..*, vol. 66, pp 3131–3138 (1994).

Fischer, U., et al., "Oxygen Tension at the Subcutaneous Implantation Site of Glucose Sensors," *Biomed. Biochim. Acta*, vol. 11/12, pp 965–971 (1989).

Frew, J.E., et al., "Electrochemical Biosensors," *Analytical Chemistry*, vol. 59, No. 15, pp 933A–944A (Aug. 1, 1987).

Gorski, W., et al., "Ruthenium Catalyst for Amperometric Determination of Insulin at Physiological pH," *J Electroanalytical Chem*, vol. 425, pp 191–199 (1997).

Gorton, L., "Carbon Paste Electrodes Modified with Enzymes, Tissues, and Cells," *Electroanalysis*, vol. 7, No. 1, pp 23–29 and 33–35.

Gough, D.A., et al., "Two–Dimensional Enzyme Electrode Sensor for Glucose," *Anal. Chem.*, vol. 57, No. 12 pp 2353–2357 (Oct. 1985).

Ho, C.S., et al., "Enhancing Penicillin Fermentations by Increased Oxygen Solubility Through the Addition of n–Hexadecane," *Biotech and Bioeng*, vol. 36, pp 1110–1118 (1990).

Kalcher, K., et al., "Sensors Based on Carbon Paste in Electrochemical Analysis: A Review with Particular Emphasis on the Period 1990–1993," *Electroanalysis*, vol. 7, No. 1, pp 5–6 (1995).

Kuhn, L.S., "Biosensors: Blockbuster on Bomb?", *Electrochem Society Interfae* (1998).

Littlejohn, D., et al., "Reviews on Analytical Chemistry—Euroanalysis VIII", *Royal Society of Chemistry*, Cambridge, Great Britain, pp 84–85 (1994).

Lowe, K.C., "Perfluorochemical Respiratory Gas Carriers: Applications in Medicine and Biotechnology," *Science Progress*, vol. 80, No. 2, pp 169–193 (1997).

Millard, R.W., "Oxygen Solubility, Rheology and Hemodynamics of Perfluorocarbon Emulsion Blood Substitutes," *Art. Cells, Blood Subs., and Immob. Biotech.*, vol. 22, No. 2, pp 235–244 (1994).

Rogers, M.J., et al., "Interaction of D–Glucal with *Aspergillus niger* Glucose Oxidase," *Biochemicstry*, vol. 10, No. 25, pp 4624–4631 (1971).

Sawyer, D.T., "Redox Thermodynamics for Oxygen Species," *Oxygen Chemistry* (1991), Oxford University Press NY USA p. 21.

Schultz, J.S., "Biosensors" *Scientific American*, pp 64–69 (Aug. 1991).

Swoboda, B.E.P., et al., "Purification and Properties of the Glucose Oxidase from *Aspergillus niger*", *J. Biological Chem.*, vol. 240, No. 5, pp 2209–2215 (May 1965).

Tallman, D.E., et al., "Composite Electrodes for Electroanalysis: Principles and Applications," *Electroanalysis*, vol. 2, pp 499–510 (1990).

UmlandJ.B., et al., "General Chemistry," *West Publ. Co.*, St. Paul, MN, pp 962–965 (1993).

Wang, J., et al., "Mixed lant Tissue–Carbon Paste Bioelectrode," *Analytical Chem*, vol. 60, pp 1545–15148 (1988).

Wang, J., et al., "Needle–Type Dual Microsensor for the Simultaneous Monitoring of Glucose and Insulin," *Anal. Chem.*, vol. 73, pp 844–847 (2001).

Wang, J., et al., "Trace Measurements of Insuline by Potentiometric Stripping Analysis at Carbon Paste Electrodes," ABSTRACT (1997).

Wang, J., et al., "Hydrocarbon Pasting Liquids for Improved Tyrosinase–Based Carbon–Paste Phenol Biosensors," *Electroanalysis*, vol. 9, No. 14, pp 1102–1106.

Wang, J., "Analytical Electrochemistry" TEXTBOOK,J. Wiley & Sons, New York US (2000), pp 123–126.

Wang, J., et al., "Highly Selective Biosensing of Glucose Utilizing a Glucose Oxidase + Rodium + Nafion®," *J. Electroanalytical Chemistri*, vol. 395, pp 287–291 (1995).

Wilhelm, E., et al., "Thermodynamic Functions of the Solubilities of Gases in Liquids at 15° C." *Chemical Reviews*, vol. 73, No. 1, p 1–9 (Feb. 1973).

Zhang, Y., et al., "In Vitro and In Vivo Evaluation of Oxygen Effects on a Glucose Oxidase Based Implantable Glucose Sensor," *Analytical Chimica Acta*, vol. 281, pp 513–520 (1993).

* cited by examiner

MICROSENSORS FOR GLUCOSE AND INSULIN MONITORING

CROSS-REFERENCE TO RELATED APPLICATIONS

This application is a continuation-in-part application of U.S. patent application Ser. No. 09/216,353, now abandoned entitled *Oxygen-Rich Oxidase Enzyme Electrodes*, to Joseph Wang and Fang Lu, filed on Dec. 18, 1998, and the specification thereof is incorporated herein by reference. This application claims the benefit of the filing of U.S. Provisional Patent Application Ser. No. 60/267,811, entitled *Needle-Type Dual Microsensor for the Simultaneous Monitoring of Glucose and Oxygen*, filed on Feb. 8, 2001, and of U.S. Provisional Patent Application Ser. No. 60/068,916, entitled *Oxygen-rich Oxidase Enzyme Electrodes*, filed on Dec. 29, 1997, and the specifications thereof are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 1 R01 RR14173-0 awarded by the U.S. Department of Health and Human Services awarded by the National Institutes of Health for the National Center for Research Resources.

BACKGROUND OF THE INVENTION

1. Field of the Invention (Technical Field)

The present invention relates to dual microsensors for the simultaneous amperometric monitoring of glucose and insulin, and to oxygen-rich composite enzyme electrodes and their use in a range of substrate concentrations and environments severely depleted in oxygen.

2. Background Art

Diabetes mellitus is a chronic metabolic disorder that results from a total or partial deficiency of insulin. In order to manage care, including providing enhanced diabetes control, there is a recognized need for glucose monitoring, including the simultaneous detection of glucose and other analytes, including most particularly insulin. Insulin sensing is of significant importance for clinical diagnosis, because it serves as a predictor of diabetes, insulinoma and trauma. By simultaneously measuring both glucose and insulin, an insulin/glucose ratio can readily be determined, thereby providing a single point assay for diagnosis of insulinoma and the management of diabetes.

It is known to utilize a ruthenium-oxide ($RuO_x$)-type catalytic film sensor for insulin detection at physiological pH. Gorski, W., Aspinwall, C., Lakey, J. R. T., Kennedy, R. T., *J. Electroanal. Chem.* 1997, 425, 191. $RuO_x$ sensors have been used, for example, to monitor insulin secretion from pancreatic β cells. However, this device cannot be used to detect glucose or other substances.

Oxidase-catalyzed enzymatic reactions play a major role in the development of enzyme-based biosensors (Clark, Jr., L. C., Sachs, G. *Ann NY Acad. Sci.* 1962, 148,133; Schultz, J. *Sci. Amer.* 1991(8), 64). The large number of commercially available oxidases opens up the prospects for the detection of important substrates (such as glucose, lactate, or cholesterol) in relevant clinical, food or biotechnological matrices.

The following reaction:

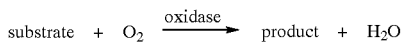

can be monitored amperometrically:

As the immobilized enzyme relies on the use of oxygen as the co-substrate, the operation of these enzyme electrodes suffers from problems due to restricted solubility of oxygen and variations in the oxygen level (Zhang, Y., Wilson, G. S. *Anal. Chim. Acta* 1993, 281,513). For example, implantable glucose sensors often suffer from low oxygen availability in subcutaneous tissue.

Common routes for minimizing the strong oxygen dependence include the replacement of oxygen with a non-physiological electron acceptor (Cass, A. E., Davis, G., Francis, G., et al., *Anal. Chem.* 1984 56, 667), or the use of a proper membrane coverage that improves the surface availability of oxygen (relative to the substrate) (Gough, D., Lucisano, J., Tse, P. *Anal. Chem.* 1985, 57, 2353; Fischer, V., Hidde, A., Herman, S., von Woedtke, T., Rebrin, K., Abel, P. *Biomed. Biochim. Acta* 1989,48,965).

Others in the field have approached the problem of a limited oxygen environment in various ways: Clark (U.S. Pat. No. 4,721,677 (1988)) relies upon an oxygen chamber with a membrane to hold oxygen extracted from the tissues; Zawodzinski et al. (U.S. Pat. No. 5,227,042 (1993)) utilizes a back supply (bubbling) of oxygen through a porous electrode; and Rishpon et al. (U.S. Pat. No. 5,082,550 (1992)) casts a perfluorosulfonic acid isomer as a film directly on the conductor surface of the electrode to supply oxygen. These approaches sometimes result in a rather bulky apparatus and cumbersome operation, and are not compatible with miniaturization. In addition, they do not address the additional problem of electroactive interferences that can strongly affect sensor output.

Others in the field who address the interference problem (but ignore the oxygen limitation problem) frequently use a platinized carbon to create a paste for the enzyme (Bennetto et al., U.S. Pat. No. 4,970,145 (1990); Maley et al., U.S. Pat. No. 5,616,222 (1997)). These methods decrease interference somewhat, but still function at higher potentials.

Carbon paste electrodes (CPEs), consisting of a mixture of graphite powder and an organic pasting liquid (commonly mineral oil), represent an attractive approach for the preparation of reagentless biosensors (Wang, J., Un, M. S. *Anal. Chem.* 1988, 60, 1545; Gorton, L. *Electroanalysis* 1995, 7,23). The pasting liquid serves not only for filling the crevices between the graphite particles, but results in an electrode that is fundamentally different from those (e.g., Pt, Au) commonly used for amperometric transduction. Common pasting liquids include mineral oil, parrafin oil, silicone grease, and bromonaphthalene.

U.S. Pat. No. 5,922,183 (1999), to Rauh, discloses a thin film matrix for detecting substances, including glucose, utilizing an enzyme biosensor, such as a glucose oxidase, and a hydrous metal oxide as a catalyst or "cofactor" in enzyme reactions. However, this approach does not provide for simultaneous detection of glucose and insulin utilizing catalytic detection of insulin.

This invention provides for a combined needle-type probe, integrating an amperometric glucose biosensor with an electrocatalytic insulin microsensor. Thus in the same needle body an insulin-sensitive $RuO_x$-modified carbon-paste microelectrode is integrated with a metalized, such as rhodinized, carbon amperometric glucose b-biosensor. Despite substantial analyte concentration differences, with mM concentrations of glucose and nM concentrations of insulin, and the use of different transduction principles, the microsensors of the invention respond independently and rapidly to the corresponding target analytes, with no apparent cross reactivity.

This invention further successfully addresses problems encountered in many in vivo and in vitro monitoring electrodes, including oxygen dependence of oxidase enzyme electrodes and redox interferences, through the use of carbon paste biosensors with oxygen-yielding (e.g. fluorochemical) pasting liquids supplied in a reservoir within the needle-type sensor. Due to the high oxygen solubility in perfluorocarbons, such pasting liquids provide an internal supply of oxygen, and efficient operation of first-generation oxidase electrodes under oxygen-deficient conditions. The result is a composite (binder serves as the oxygen reservoir) bioelectrode that provides real-time in vivo or ex vivo, accurate monitoring of specific chemical environments within the body.

SUMMARY OF THE INVENTION
(DISCLOSURE OF THE INVENTION)

The invention includes an apparatus for producing signals related to the concentrations of both glucose and insulin, the apparatus including a first conductive composite including glucose oxidase and a metal posited within a first cylindrical tube; a second conductive composite including a metal oxide catalyst posited within a second cylindrical tube; a sleeve containing the first cylindrical tube and the second cylindrical tube; a first electrical contact within the first cylindrical tube in contact with the first conductive composite; and a second electrical contact within the second cylindrical tube in contact with the second conductive composite. In this apparatus, the first conductive composite can include a carbon powder conductor. The metal used in the first conductive composite can include rhodium, iridium, or ruthenium. The sleeve can optionally include a conductor, and can further include an insulating layer posited on the exterior the sleeve with a conducting layer posited on the insulating layer. The metal oxide catalyst used in the second conductive composite can include $RuO_x$ or $IrO_x$. In one embodiment, the first cylindrical tube and the second cylindrical tube have an interior diameter of less than 500 Mm. The first conductive composite can include an oxygen-rich binder, which oxygen-rich binder may be a perfluorochemical, myoglobin, or hemoglobin. The perfluorochemical can include polychlorotrifluoroethylene.

In another embodiment, the invention provides an apparatus for producing a signal related to the concentration of a substance, the apparatus including a conductive composite including an oxygen-dependent enzyme and sufficient oxygen-rich binder to support an oxygen-dependent enzymatic reaction in the absence of exogenous oxygen; a sleeve with a first end and second end; a cavity disposed within the first end of said sleeve wherein the length of the sleeve is at least about 0.2 mm, said cavity containing said composite and forming an electrode end of said composite at the first end of said sleeve; and an electrical contact disposed within the second end of said sleeve extending into said cavity; wherein the ratio of the surface area of the electrode end of the composite to the volume of the composite is at least about 1:8. In this apparatus, the conductive composite can include a metal powder conductor. In another embodiment, the conductive composite can include a carbon powder conductor, including but not limited to a metalized graphite. The metalized graphite can include rhodium, iridium, or ruthenium. In the apparatus, the sleeve can include an insulator, which insulator may include polytetrafluoroethylene. In the apparatus, the cavity can include a diameter of between approximately 0.2 mm and approximately 5.0 mm, including a diameter of about 2.0 mm. The oxygen-rich binder can include a perfluorochemical, myoglobin, or hemoglobin, and in one embodiment a d perfluorochemical including polychlorotrifluoroethylene. The oxygen-dependent enzyme can include an oxidase enzyme, such as glucose oxidase. The apparatus can further include a protective membrane covering at least a portion of the electrode end conductive composite. This membrane may include polyurethane, polycarbonate, polyethylene glycol, polyvinyl chloride or polyhydroethylmethacrylate, and may further optionally include an oxygen-rich film, such as a film including Pluronic F-88 or a perfluorosulfonate isomer. The sleeve of the apparatus may include a needle.

The invention further provides a method of simultaneous detection of glucose and insulin in a liquid sample, the method including the steps of providing a first biosensor including glucose oxidase; providing a second biosensor including a metal oxide catalyst; simultaneously placing the first biosensor and the second biosensor in the liquid sample; applying a detection potential to the first biosensor and the second biosensor; detecting a biocatalytic signal at the first biosensor; and detecting an electrocatalytic signal at the second biosensor. The detecting steps may include amperometric detection or stripping potentiometry. The metal oxide catalyst can include $RuO_x$ or $IrO_x$. The first biosensor may, in certain embodiments, include an oxygen-rich binder. In one embodiment, the first biosensor and second biosensor are placed within a common sleeve or housing, including a needle.

The invention further provides a method of detecting substrate concentration of an environment using a composite biosensor, the method including the step of providing a biosensor comprising a conductive composite comprising sufficient oxygen-rich binder to support an oxygen-dependent enzymatic reaction in the absence of exogenous oxygen, a conductor, an oxygen-dependent enzyme, a reservoir containing the composite, and an electrode end of the composite, wherein the ratio of the surface area of the electrode end of said composite to the volume of said composite is at least about 1:8, placing the biosensor in the environment, and detecting the substrate concentration.

The invention also provides a method of detecting substrate concentration of an environment using a composite biosensor, the method comprising providing a biosensor comprising a conductive composite comprising an oxygen-rich binder, a conductor, an enzyme, and a reservoir to hold the composite, placing the biosensor in the environment, and detecting the substrate concentration.

A primary object of the present invention is to provide a dual sensor for simultaneous detection of both glucose and insulin utilizing a patient blood or other bodily fluid specimen.

Another object of the present invention is to provide a dual sensor wherein glucose is detected by means of biocatalytic action of glucose oxidase and insulin is detected by means of electrocatalytic activity of ruthenium oxide.

Another object of the present invention is to provide a dual sensor that provides accurate readings for triggering proper alarms and making valid therapeutic decisions.

Another object of the present invention is to utilize perfluorochemicals in a bioelectrode to provide an internal oxygen source.

Yet another object is to provide an interference-free bioelectrode for use in oxygen-deficient environments.

A primary advantage of the present invention is that it provides for simultaneous measurement of both glucose and insulin, utilizing different but compatible transduction principles.

Another advantage of the present invention is that it provides a miniature, needle-type dual sensor that may be employed as an implantable sensor.

Another advantage is the lack of need for an exogenous oxygen source or supply.

Another advantage of the present invention is the increased accuracy and selectivity due to lessened interference.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION

A dual sensor is provided for the simultaneous amperometric monitoring of glucose and insulin, wherein the glucose probe is based on the biocatalytic action of glucose oxidase, and the insulin probe is based on the electrocatalytic activity of ruthenium oxide. In one embodiment, the dual sensor is miniturized, such that both electrodes, formatted as carbon-paste working electrodes, may be inserted into a 14-guage needle. Under flow injection conditions the dual sensors exhibit very rapid response to dynamic changes in the concentrations of both glucose and insulin. No apparent cross reactivity is observed in mixtures containing millimolar (mM) glucose and nanomolar (nM) insulin concentrations. The response is linear, to at least 1000 nM insulin and 14 mM glucose, and reproducible.

Figure 1:
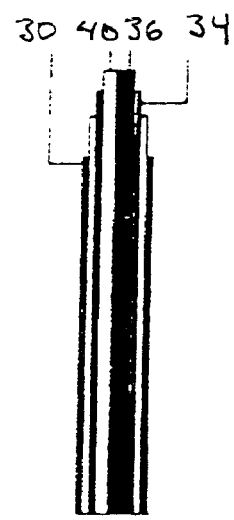
FIG. 1 is a schematic drawing of a preferred embodiment of the integrated needle-type glucose/insulin microsensor of the present invention.
Figure 1:
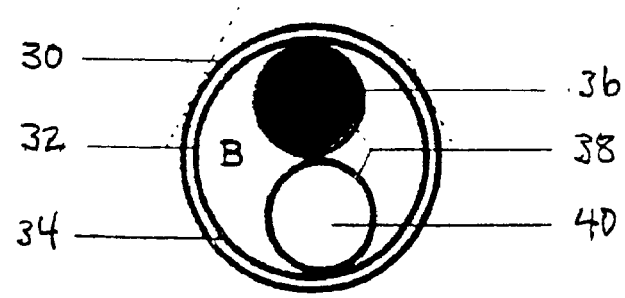
Figure 1:
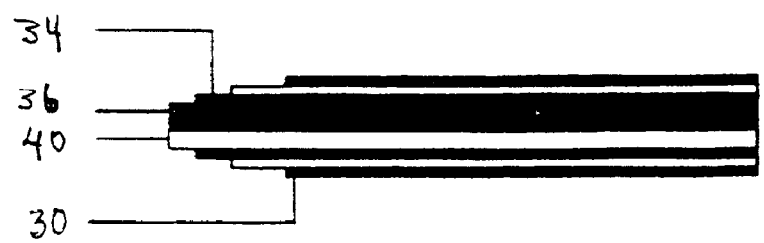

FIG. 1 shows a preferred embodiment of the invention, a schematic of an integrated needle-type glucose and insulin microsensor. As shown in FIG. 1A, stainless steel needle body 34 encloses glucose sensor 36 and insulin sensor 40. Stainless steel needle body 34 serves as the reference electrode for glucose sensor 36, while Ag/AgCl layer 30 serves as the reference electrode for insulin sensor 40. FIG. 1B depicts a cross sectional view of the sensor tip. Shown are Teflon® tubing walls 38 that enclose glucose sensor 36 and insulin sensor 40. Stainless steel needle body 34 has insulating layer 32 posited over the exterior thereof, with Ag/AgCl layer 30 over insulating layer 32.

Glucose sensor 36 may conventionally be a glucose enzyme microelectrode. A metallized carbon-paste glucose microelectrode is prepared, such as by mixing 10 mg of glucose oxidase with 100 mg of rhodium-containing carbon paste, made from 40% rhodium-on-carbon, containing 5% rhodium, and 60% mineral oil, w/w. The paste is packed into the end of a 7 cm long Teflon® tube, with a 250 $\mu$m interior diameter and 600 $\mu$m outside diameter. The paste filled the tip to a height of 5 mm, with electrical contact to the inner end made with a 0.2 mm diameter copper wire.

Insulin sensor 40 may conventionally be an insulin-sensitive $RuO_x$-modified electrode. A carbon paste is made by mixing 70% graphite powder, riot containing any metal, with 30% mineral oil, w/w, for approximately 20 minutes. A 7 cm long tube with a 250 $\mu$m interior diameter and 600 $\mu$m outside diameter is filled with the paste to a height of 5 mm, with electrical contact to the inner end made with a 0.2 mm diameter copper wire. The resulting carbon paste microelectrode is then electrochemically treated in 0.1 M $KNO_3$ medium by polarizing at 1.8 V against Ag/AgCl (3 M KCl) for thirty seconds, followed by scanning the potential between −1.0 and 1.6 V at 100 mV/second for ten cycles, all in the same solution. The electrode was then rinsed, and the $RuO_x$ film electrochemically deposited. The $RuO_x$ film is electrochemically deposited on the carbon paste electrode surface from a 0.3 mM $RuCl_3$ and 10 mM $HClO_4$ solution, by cycling potential between −0.8 and 0.65 V at 10 V/second for twenty-five minutes. Electrode modification is initiated immediately upon dissolving the $RuCl_3$ in the $HClO_4$ solution. The electrochemical deposition was conducted using a three-electrode system, with an Ag/AgCl reference electrode and a platinum wire counter electrode.

The surface of a 14-gauge stainless steel needle was coated with an insulation ink to form thin film insulating layer 32, with an approximately thickness of 50 µm. Insulating layer 32 was cured at 110° C. for 30 minutes. Ag/AgCl layer 30 was coated on insulating layer 32 and cured for 30 minutes in an oven. Glucose sensor 36 and insulin sensor 40 are then inserted into the needle body.

In alternative embodiments, the selectivity and stability of electrocatalytic insulin microsensors can be increased. While metal-oxide catalysts, such as $RuO_x$ and $IrO_x$ are highly sensitive and permit rapid detection of nM insulin levels, there is the potential of interference from other oxidizable constituents of biological fluids. Due to the large size of the insulin target, common permselective coatings, such as those based on size or charge exclusion, cannot be used for preferential transport of insulin. However, hydrophobic lipid layers may be employed as a permselective coating, permitting transit of insulin but not other potentially interfering substances. Thus in one embodiment a mixed phospholipid and cholesterol film is employed, which is highly effective at rejecting small hydrophilic molecules, such as ascorbate, acetaminophen or urete, while allowing the transport and detection of large biomolecules, such as insulin. In addition, cholesterol doping of a phospholipid film imparts significant mechanical stability to such film. Thus the metal-oxide catalyst layer, such as electrochemically deposited $RuO_x$, may be covered with a lipid film, including a phospholipid film containing cholesterol. Alternatively, $RuO_x$, or another suitable metal-oxide catalyst, may be dispersed with a permselective layer, which layer includes a phospholipid film, optionally containing cholesterol. The film thickness and phospholipid/cholesterol ratio may be varied, thereby varying one or more parameters, such as insulin response time, dynamic range, insulin/interferant discrimination and operational stability/surface protection.

In an alternative embodiment, stripping protocols may be employed for measurement of insulin and glucose levels. This measurement protocol may be employed with dual sensor test strips. The majority of personal blood glucose meters utilize a disposable, generally screen-printed, enzyme electrode test strips, produced by thick-film microfabrication technology. A dual glucose and insulin test strip can couple common chronoamperometric measurements of glucose with highly sensitive stripping detection of insulin. Adsorptive stripping protocols may be employed with cartoon electrodes to measure insulin levels, including single-use thick-film carbon transducers. Different carbon inks, printing and activation conditions, as well as relevant variables of the stripping protocol, such as accumulation potential and time, stripping mode and environmental conditions, may be employed. Solution pH, ionic strength and the interfering effect of biomacromolecules can also be examined.

The invention further provides an oxygen-dependent enzyme carbon paste electrode (CPE) having an internal oxygen binder that can be utilized in low oxygen environments with little effect from interference. The invention addresses two problems encountered with electrodes used in oxygen-depleted environments. The first problem addressed is that of oxygen demand. It is well known that the solubility of oxygen in some organic solvents is many times greater than in water (Umland, J. General Chemistry, 1st Ed, West Publishing Co., St Paul, 1993, p. 962; Wilhelm, E., Battino, R. Chem Reviews, 1973, 73, 1). In particular, due to the very high oxygen solubility in fluorochemicals (resembling that of hemoglobin), such solvents have been used as oxygen transporters and blood substitutes in humans and animals (Clark, Jr., L. C., Gollan, F. Science 1966, 152, 1755; Ho, C., Ju, L. Baddour, R. Biotechnol. Bioeng. 1990, 38,1110; Millard, R. W. J. Artificial Cells Blood Substitutes Immobil. Biotech. 1994, 22,235). Taking advantage of this remarkable oxygen solubility, the invention uses novel oxygen-insensitive first-generation oxidase electrodes based on fluorochemical carbon pastes (or other biocomposites based on oxygen-rich binders).

A preferred embodiment of the present invention, the fluorocarbon binder polychlorotrifluorethylene (Kei-F) fulfills the role of satisfying oxygen demand internally, thus eliminating the signal dependence on oxygen level, and also allows for a convenient paste preparation (unlike perfluorononane, which is too dry and requires a large liquid to carbon ratio). Binders other than Kel-F may also be used. For example, mineral oil may be used in combination with a perfluorochemical (such as Nafion), although mineral or oil alone does not provide a sustainable source of oxygen, and results in a rapid glucose response loss within the first 20 minutes. The oil binder may also contain a different additive (such as myoglobin, a natural oxygen binder) with or without the presence of perfluorocarbons.

In one embodiment, the ratio of surface area of the electrode to volume of the carbon paste electrode is at least about 1:8. For cylindrical electrodes, this may be determined by simple formulas for the volume of the cylinder (using the standard formula $V=\pi r^2 h$, where r is the radius and h is the height), with area of the electrode surface similarly determined. Thus the ratio of the surface areas (as in $mm^2$) to the total volume of the electrode (as in mm), such as a carbon paste electrode, is at least about 1:8. This provides a sufficient volume of internal oxygen binder to conduct measurements in an oxygen-depleted environment, wherein the sole source of oxygen for the oxygen-dependent enzymatic reaction is the internal oxygen binder. For example, assume a 2 mm diameter electrode, which would consume about $6\times10^{-11}$ M/minute of oxygen in an enzymatic reaction, assuming that the applied current reflects about 10% of the resulting peroxide product. Based on an effective oxygen solubility in fluorocarbon oil of around 6 mM, the amount of stored oxygen for an 8 mm high cylindrical-shaped electrode would be about $1.2\times10^{-7}$ M, thereby providing sufficient oxygen for over 40 hours of actual operation. Smaller ratios than 1:8 may also employed in the invention; for example, a 2 mm diameter electrode in a 2 mm high cylindrical-shaped electrode would still have about $4\times10^{-8}$ M stored oxygen, sufficient for over about 40 hours of operation. However, the method of this invention must be distinguished from applications wherein a coating or thin layer is provided which, even if including a fluorocarbon, would contain only sufficient oxygen to support an oxygen-dependent enzymatic reaction, in the absence of endogenous oxygen, for a few seconds or at most, a few minutes. Oxygen consumption depends on the quantity of oxygen-dependent enzyme exposed to the analyte, and this in turn is directly related to the surface area of the electrode. With a small surface area a correspondingly small quantity of enzyme is exposed to analyte. Thus small surface area electrodes, with large reservoirs containing oxygen-rich binder, may be employed in environments which otherwise contain no oxygen.

Stabilization of the enzyme in a carbon paste environment is of major significance in view of the limited stability of enzyme electrodes at human physiologic temperatures (Frew, J., Hill, H. A. *Anal. Chem.* 1987, 59,933A–938A). The carbon paste electrodes enhance thermal stability and storage life, and allow for a prolonged high-temperature (e.g. 60° C.) stress.

A second problem addressed by the present invention in conjunction with the oxygen dependence problem is the interference to the signal provided by electroactive substances such as acetaminophen, ascorbic acid, salicylic acid, and some amino acids. The present invention uses electrocatalytic metal-dispersed materials to eliminate redox interferences. Metalized carbon bioelectrodes allow quantitation of a signal over the entire potential range, versus mediator-based sensor, which starts at 0.0 V. A preferred embodiment of the invention uses rhodium, or alternatively, ruthenium, dispersed within the carbon paste to allow signal detection at low potentials where interfering reactions are eliminated. These carbon paste compounds shift the detection potential for hydrogen peroxide to near zero volts. The enhanced catalytic action of these metal-laden pastes, compared to pure metal surfaces, is due to the three-dimensional distribution of metal sites within the plastic matrix. Microporosity leads to a preferential access of small particle species towards catalytic centers.

Because the enzyme is incorporated into the carbon paste, and as the need for anti-interference and diffusion limiting membrane is eliminated, at most only a protective biocompatible coating is needed for the bioelectrode, thus reducing the complexity of the apparatus. The coating can be purely protective, such as polyethylene oxide, polyurethane, polycarbonate, polyvinyl chloride, or polyhydroxyethylmethacrylate. Alternatively, it may also contain an oxygen-rich film, such as Pluronic F48 or Nafion.

Figure 6:
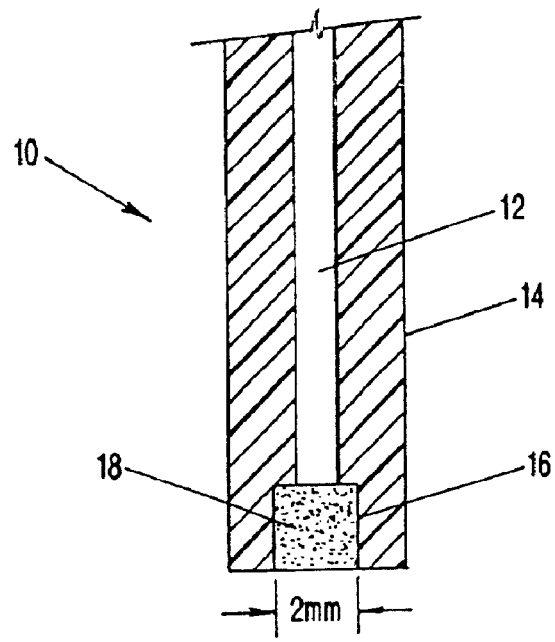
FIG. 6 is a cross-sectional view of a preferred embodiment of the rotating or stationary disc carbon paste amperometric glucose-detection electrode of the present invention.

FIG. 6 shows a preferred embodiment of the invention, macro rotating or stationary disc carbon paste electrode 10 for use in in vitro clinical or industrial settings. Electrode 10 comprises electrical contact 12 within cylindrical insulating sleeve 14. Sleeve 14 is preferably made of plexiglas or polytetrafluoroethylene. Contact 12 extends into cavity 16 that has a diameter of 0.2–5.0 mm, and preferably about 2.0 mm. Cavity 16 is filled with the enzyme-modified carbon paste 18 made of graphite powder and an oxygen-rich binder.

Figure 7:
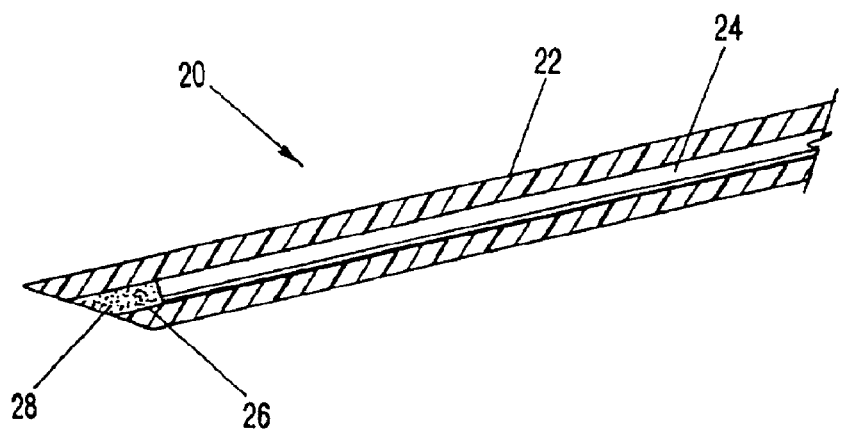
FIG. 7 is a lengthwise cross-sectional view of an alternative embodiment of an in vivo needle-type carbon paste amperometric glucose-detection electrode of the present invention.
Figure 8B:
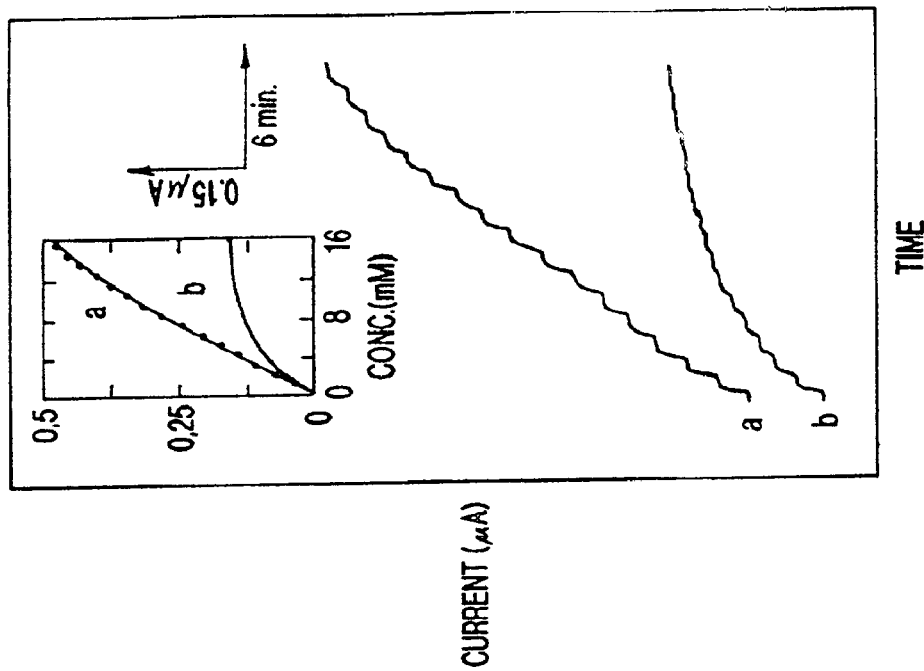
FIG. 8 is a series of graphs showing current-time recordings for successive increments of glucose obtained in the presence (a) and absence (b) of oxygen for poly (phenylenediamine)(PPD)/glucose-oxidase(GOx)-coated platinum electrode (A), GOx-modified carbon paste electrodes with mineral oil (B), with mineral oil/Nafion (C) and Kel-F oil (D) binders.
Figure 8A:
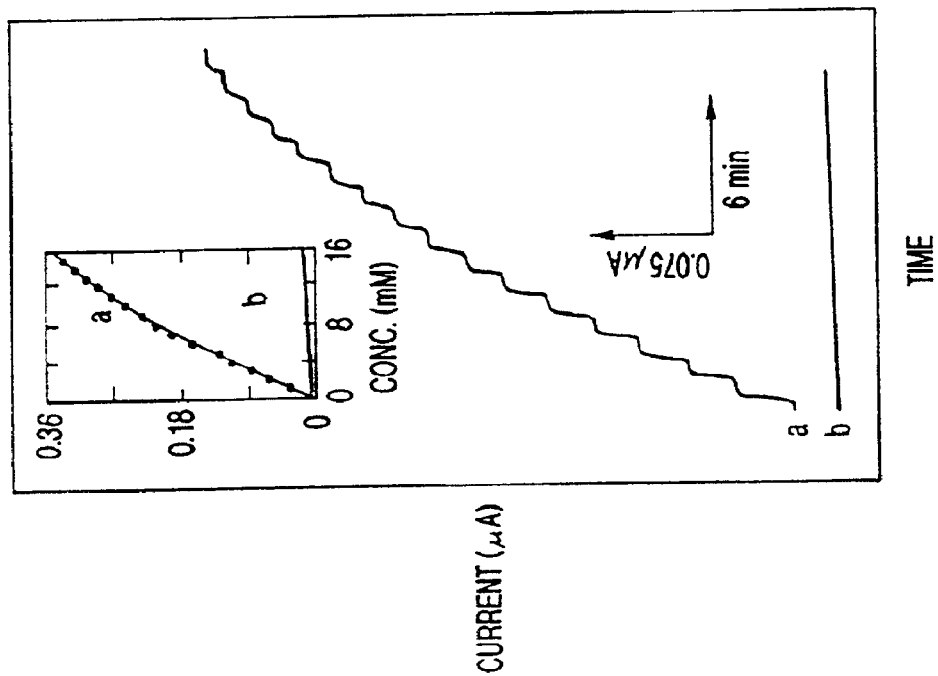
Figure 8D:
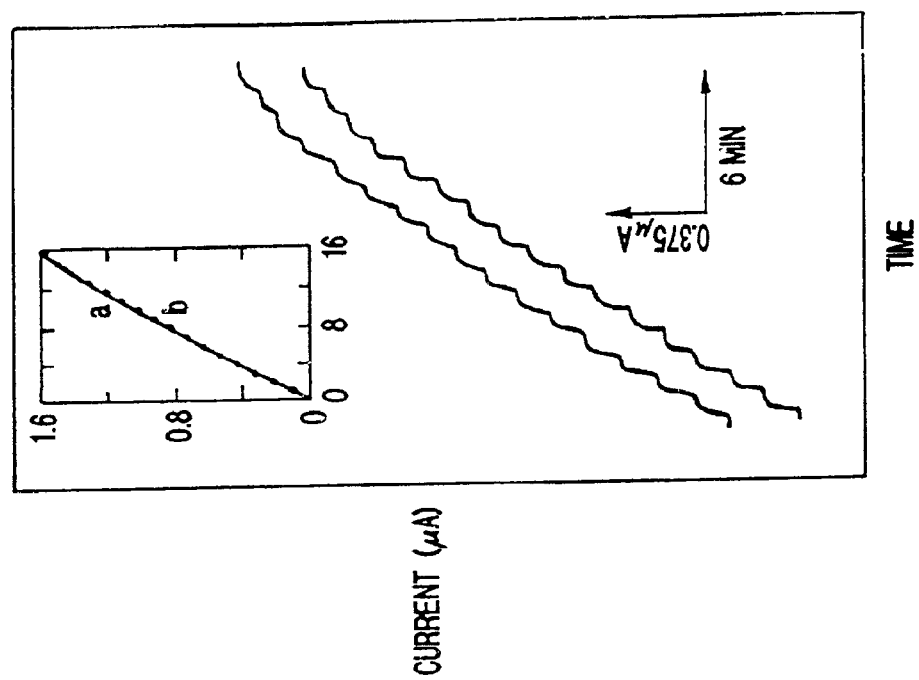
Figure 8C:
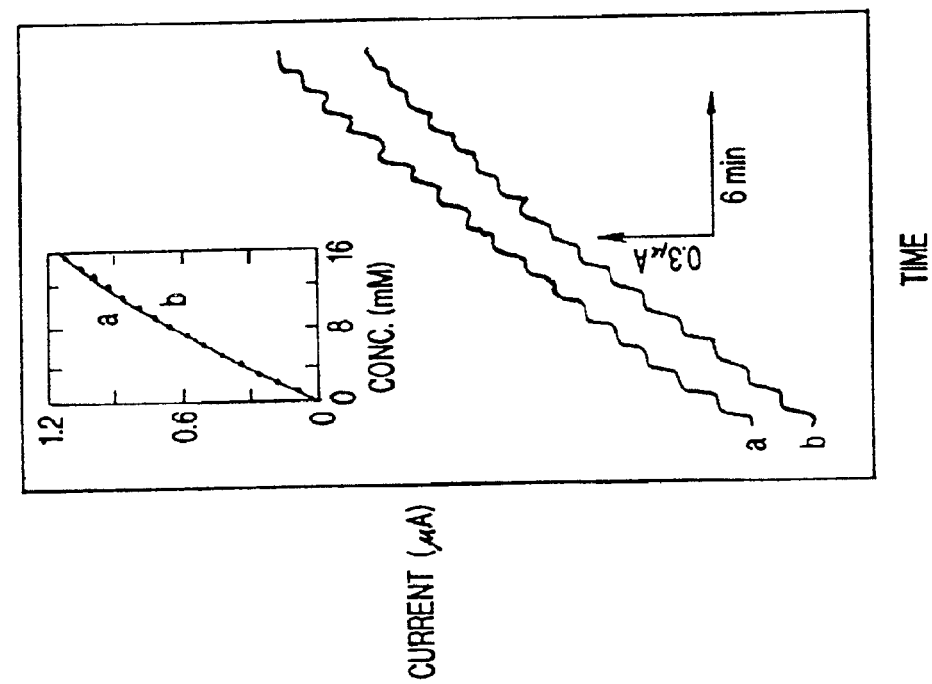

FIG. 7 shows an alternative embodiment of sensor 20 as a needle-type carbon paste electrode for implantable in vivo use. Sensor 20 comprises flexible needle 22, such as a 28-gauge needle. The inside of needle 22 is coated with an insulating material, preferably polytetrafluoroethylene. Within needle 22 is electrical contact 24. Contact 24 extends into reservoir 26, where carbon paste 28 is packed. The reference electrode (not shown) may be either integrated or separated from needle 22.

Industrial Applicability

The invention is further illustrated by the following non-limiting examples.

EXAMPLE 1

Cyclic voltammetry was conducted using a modular electrochemical system, with flow injection amperometric data collected using voltammetric analyzers with recorders. A standard flow injection system was utilized. Currents were measured in two electrode systems, with stainless steel and Ag/AgCl serving as reference electrodes for glucose and insulin measurements, respectively. Voltages are against the relevant reference electrode.

Figure 2:
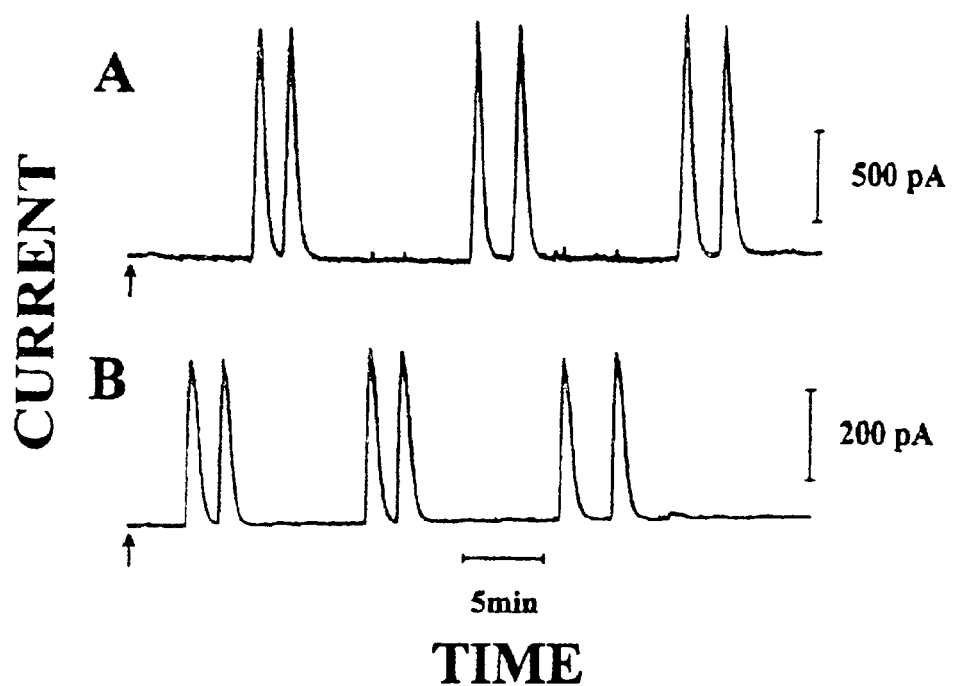
FIG. 2 is a graph showing amperometric response to alternating flow injections containing 5 mM glucose (A) and 400 nM insulin (B) utilizing the integrated needle-type glucose/insulin microsensor of the present invention.

FIG. 2 depicts dual channel flow injection current and time profiles at the needle detector of FIG. 1 for alternating injections of 5 mM glucose (A) and 400 nM insulin (B). The applied potential for both sensors was +0.6 V against stainless steel, for the glucose sensor, and against Ag/AgCl, for the insulin sensor. The carrier solution was 0.1 M NaCl and 0.05 M phosphate buffer at pH 7.4, with a flow rate of 0.5 mL per minute. Both glucose sensor 36 and insulin sensor 40 responded rapidly to injections of the target analytes, with nearly instantaneous rise in current, a somewhat slower decay, and peak widths of approximately 90 seconds. Despite the substantial difference in concentrations and use of the same operating potential, there was no apparent cross reactivity.

EXAMPLE 2

The concentration of $RuO_x$ and plating time in the electrochemical deposition were determined. Insulin response increased rapidly with the $RuO_x$ plating time up to a plating time of about ten minutes, and leveled off at a plating time of about above twenty minutes. The effect of detection potential was also determined. Insulin anodic response started at +0.3 V, rose sharply to about +0.55 V, and leveled off at higher values. Reported data was obtained utilizing a 25 minute $RuO_x$ plating time and a detection potential of +0.6 V.

EXAMPLE 3

Figure 3:
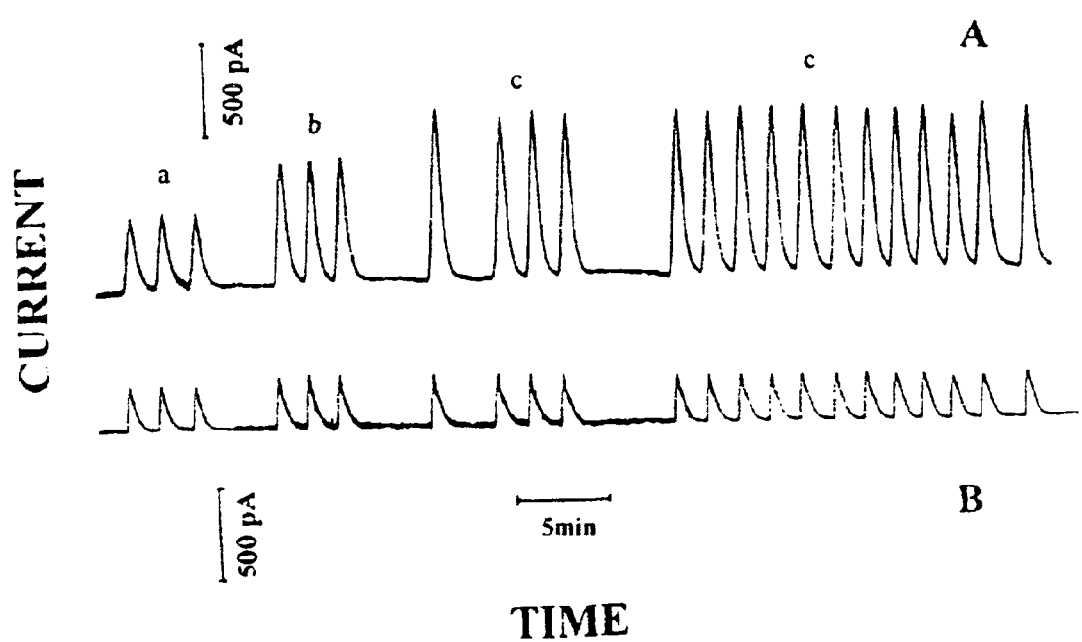
FIG. 3 is a graph showing amperometric response to simultaneous flow injections containing glucose (A) at 3 mM (a), 5 mM (b) and 7 mM (c) concentrations with insulin (B) at 200 nM concentration, utilizing the integrated needle-type glucose/insulin microsensor of the present invention.

FIG. 3 shows the simultaneous response to glucose (A) and insulin (B) in mixtures containing varying concentrations of glucose and a fixed concentration of insulin. Operating conditions were as described for Example 1. The glucose signal increased linearly with the concentration over a 3 to 7 mM range, without influencing response for the 200 nM insulin. Additionally, both glucose and insulin signals, for a series of twelve repetitive injections, were highly consistent, demonstrating reproducibility. The mean peak current for glucose peaks (A) was 860 pA and a relative standard deviation of 2.6%, and for insulin peaks (B) was 243 pA, with a relative standard deviation of 4.1%.

EXAMPLE 4

Figure 4:
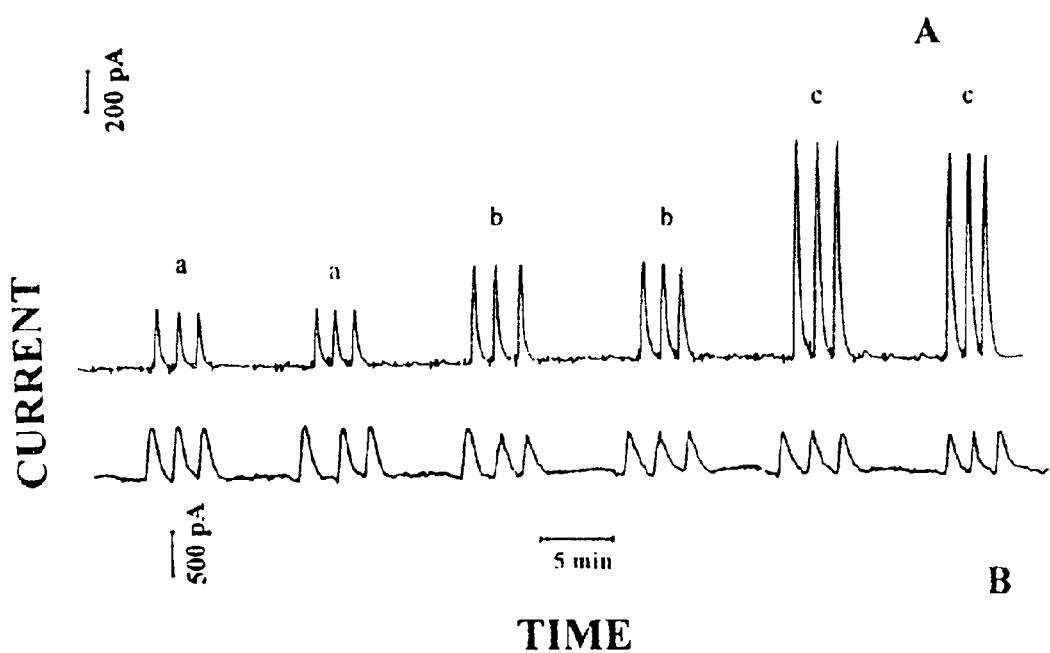
FIG. 4 is a graph showing amperometric response to simultaneous flow injections containing insulin (A) at 300 nM (a), 500 nM (b) and 1200 nM (c) concentrations with glucose (B) at 2 mM concentration, utilizing the integrated needle-type glucose/insulin microsensor of the present invention.

FIG. 4 shows the simultaneous response to insulin (A) and glucose (B) in mixtures containing varying concentrations of insulin and a fixed concentration of glucose. Operating conditions were as described for Example 1. The insulin signal increased linearly with the concentration over a 300 to 1200 nM range, without influence response for the 2 mM glucose.

EXAMPLE 5

Figure 5:
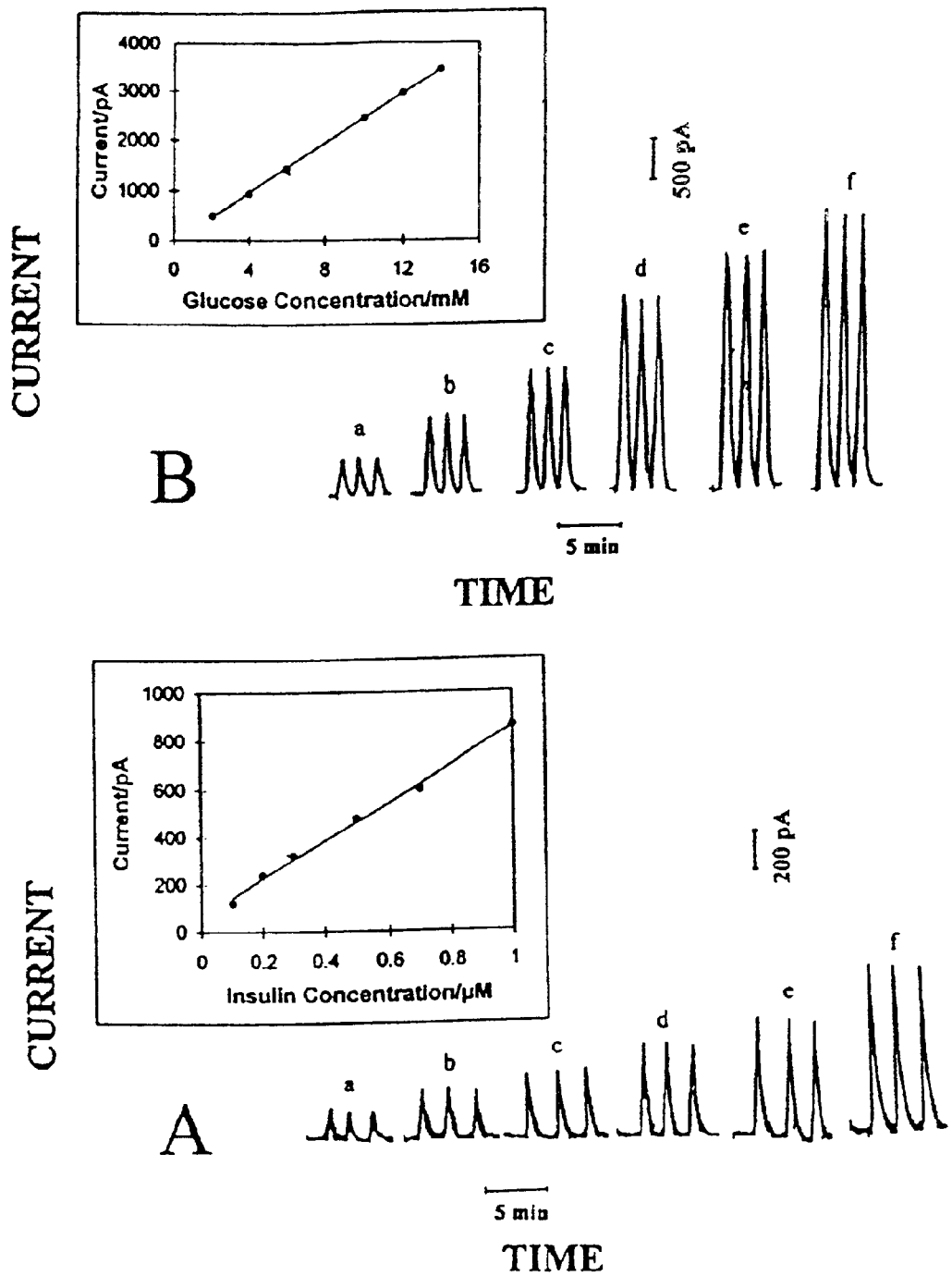
FIG. 5 are graphs showing (A) response to increasing levels of insulin at 100 nM (a), 200 nM (b), 300 nM (d), 700 nM (e) and 1000 nM (f concentrations and (B) response to increasing levels of glucose at 2 mM (a), 4 mM (b), 6 mM (c), 10 mM (d), 12 mM (e) and 14 mM (f) concentrations, together with insets depicting the resulting calibration plots.

FIG. 5 shows flow injection calibration data for insulin (A) and glucose (B) over a concentration range of 100 to 1000 nM for insulin and 2 to 14 mM for glucose. The response peak for both analytes increased proportionally to the concentration, yielding highly linear calibration plots, shown as inserts. The sensitivity for insulin was 875 pA/$\mu$M and for glucose was 245 pA/$\mu$M. Detection limits of 50 nM insulin and 0.4 mM glucose were estimated on the basis of the signal-to-noise characteristics of the data.

EXAMPLE 6

Stability of the needle detector of FIG. 1 was examined over a ten-day period, with use of the same surfaces and intermittent storage at 4° C. The glucose sensor displayed a negligible decrease of about 8% to 6 mM glucose, while the insulin sensor was highly stabile for the first three days, with a gradual daily decay of about 4%.

EXAMPLE 7

Experiments relating to an oxygen-rich binder were carried out with the BAS CV-27 volammetric analyzer (BAS, W. Lafayette), in connection with a BAS X-Y-t recorder. The enzyme electrode, reference electrode (Ag/AgCl, Model RE-1, BAS), and platinum wire auxiliary electrode joined the 10 mL cell (Model VC-2, BAS) through holes in its Teflon cover. A magnetic stirrer provided the convective transport during the amperometric measurement.

Enzyme electrodes were prepared by mixing 10 mg of glucose oxidase (GOx) with 100 mg carbon paste containing 75% Kel-F oil (poly(chlorotrifluoroethylene)) and 25% graphite powder (Rh-on-C, Aldrich, Milwaukee, Wis.). Mixing proceeded for an additional 30 minutes. A portion of the resulting paste was packed tightly into the cavity (3 mm diameter, 2 mm depth) of a BAS voltammetric electrode (Model MF-2010). The electrode surface was smoothed on a weighing paper. Carbon paste biosensors based on other pasting liquids or formulations were prepared in a similar fashion. The Kel-F/GOx-carbon paste microelectrode was prepared by packing the paste into the end of a on long Teflon tube (0.2 mm i.d., 0.6 mm o.d.). The paste filled the tip to a height of 8 mm, with electrical contact to its inner end made with a 0.1-mm diameter copper wire.

All solutions were prepared from double-distilled water. Glucose, glucose oxidase (EC 1.1.3.4, Type X-S, *Aspergillus Niger*, 135,000 U/g), o-phenylenediamine, sodium acetate and glucose (all reagent grade from Sigma (St. Louis, Mo.) were used without further purification. Kel-F oil (#10) was purchased from Ohio Valley Specialty Chemical (Marietta, Ohio). The rhodium-on-carbon (5% Rh), mineral oil, heptane and perfluorosulfonate (Nafion) (Aldrich, Milwaukee, Wis.) solution (5% by weight in a mixture of lower aliphatic alcohols and water, ER 1,100) were obtained from Aldrich. The paraffin oil (PX0047-1) and dodecane (DX24151) were purchased from EM Science. All measurements were performed in a 0.05 M phosphate buffer solution (pH 7.4).

Oxygen removal was accomplished by purging the solution with helium for 40 minutes; a helium atmosphere was subsequently maintained over the solution. There was thus no source of oxygen present other than as contained in the CPE. Experiments were performed by applying the desired potential (usually +0.06 V), stirring the solution at 300 rpm, allowing the transient background current to decay to a steady-state value (in the presence of the blank solution), and spiking the glucose substrate. All experiments were conducted at room temperature.

EXAMPLE 8

A preferred embodiment of the invention was used with glucose oxidase as the enzyme. Other oxidase enzymes may also be used in the invention, e.g. lactate oxidase aid cholesterol oxidase.

FIG. 8 compares the amperometric response to successive additions of $10 \times 10^{-3}$ M glucose as obtained in the presence (a) and absence (b) of oxygen, using conventional polymer-based (A) and carbon-paste (B) enzyme electrodes, and utilizing fluorochemical-containing carbon paste bioelectrodes (C, D). The pastes were prepared by mixing 10 mg of GOx within 100 mg carbon paste containing 40% graphite powder (Rh-on-C), and 60% pasting liquid. A 75:25 oil:graphite ratio was employed in the Kel-F paste (D), while Nafion (5% in ethanol) was mixed with mineral oil for the mineral oil/Nafion paste. The polymer-based biosensor was prepared by growing the PPD/GOx (polyphenylenediamene/ glucose oxidase) layer electrochemically for 15 minutes at +0.65 V using a quiescent solution containing 5 mM o-phenylenediamine and 1000 U/mL GOx. The disk electrode diameter was 3 mm, operating potential set at +0.6 V (vs. Ag/AgCl), in a 10 ml phosphate buffer (0.05 M, pH 7.4) solution, stirred at 300 rpm.

As expected for oxygen-deficit conditions, the polymer-entrapped enzyme electrode did not respond to the substrate additions (A,b), while the mineral-oil carbon paste biosensor displayed greatly reduced signals (B,b). In contrast, the inclusion of the perfluoropolymer Nafion in the mineral oil (C) or use of the Kel-F (poly(chlorotrifluoroethylene)) oil binder (D) dramatically minimized this oxygen dependence, and resulted in a similar response for nondeaerated and helium-saturated solutions. This thus demonstrates that the sole source of oxygen utilized by the oxygen-dependent enzyme was as included in perfluorpolymer Nafion, or in the Kel-F.

Despite the absence of oxygen, no reduction in the upper limit of linearity of the fluorocarbon-based electrodes was observed, with linearity prevailing up to about $1 \times 10^{-2}$ M, and only a slight curvature thereafter. Apparently, these oxygen-rich fluorocarbon environments supply sufficient oxygen to satisfy the enzymatic reaction even under severe oxygen deprivation. Indeed, the Kel-F/GOx carbon paste electrode displayed a total oxygen independence up to a glucose concentration of $4 \times 10^2$ (not shown). Such oxygen independence is superior to that of most effective mediators (ferrocene) or wired (osmium) bioelectrodes, which display some oxygen competition for the enzyme. A nearly oxygen independence was obtained also using perfluorononane ($CF_3$ $(CF_2)_7CF_3$) as pasting liquid, but the resulting paste was dry and required a large liquid/graphite ratio (10:1).

While the solubility of oxygen within fluorocarbons in approximately 25-fold higher than in water, oxygen solubilities in short-chain hydrocarbons are about 10 times higher than in water, and two-fold larger than in mineral oil (Wilhelm, E., Battino, R. *Chem. Reviews* 1973, 73,1; Lowe, K. D. *Science Progress* 1997, 80, 169; Sawyer, D. "*Oxygen Chemistry*", Oxford University Press, New York, 1991, p. 21). Hence, carbon-paste enzyme electrodes based on heptane or dodecane pasting liquids displayed a greatly reduced oxygen dependence in comparison to their mineral oil counterpart (not shown). However, their oxygen insensitivity was inferior to that of fluorocarbon-based biosensors. Perfluorochemicals are not saturable and can dissolve 50% of their volume with oxygen. Overall, the Kel-F CPE displayed the most favorable oxygen independence, sensing performance and surface consistency.

Lineweaver-Burke plots for the different fluorocarbon and hydrocarbon carbon paste biosensors were essentially linear (for glucose concentration in the range 5 to 60 mM, with and without oxygen; not shown). The resulting values of maximum current ($I_{max}$) and apparent Michalis-Menten constant ($K_{m,app}$) are shown below in Table 1.

TABLE 1

Kinetic Parameters of Carbon Paste Glucose Biosensors based on Different Pasting Liquids

| Pasting liquid | $K_{m,app}$ (mM) | | $I_{max}$ (µA) | |
| --- | --- | --- | --- | --- |
| | Non-deaerated sample | Deaerated sample | Nondeaerated sample | Deaerated sample |
| Mineral oil | 27.4 | 24.5 | 1.1 | 0.3 |
| Silicone grease | 35.9 | 25.1 | 1.1 | 0.2 |
| Dodecane | 41.5 | 40.2 | 2.4 | 1.8 |
| Heptane | 42.8 | 43.1 | 5.2 | 4.5 |
| Kel-F oil | 49.3 | 52.5 | 6.9 | 6.5 |
| Perfluorononane | 49.4 | 49.2 | 12.1 | 12.0 |
| Mineral oil/Nafion(1:2) | 38.6 | 35.5 | 1.6 | 1.3 |

While similar $K_{m,app}$ and $I_{max}$ values were observed for the fluorocarbon and hydrocarbon CPEs under helium and air saturation, significantly different values were indicated for the ordinary (polymer and mineral oil) bioelectrodes. The higher values of $K_{m,app}$ (>35 mM) at the fluorocarbon and hydrocarbon bioelectrodes, in comparison with that (26 mM) of the soluble enzyme (Rogers, M. J., Brandt, KG. *Biochemistry* 1971, 10,4624; Swoboda, B., Massey, V. J. *Biol. Chem.* 1965, 240, 2209), indicated that their response is controlled partly by mass transport.

EXAMPLE 9

Figure 9B:
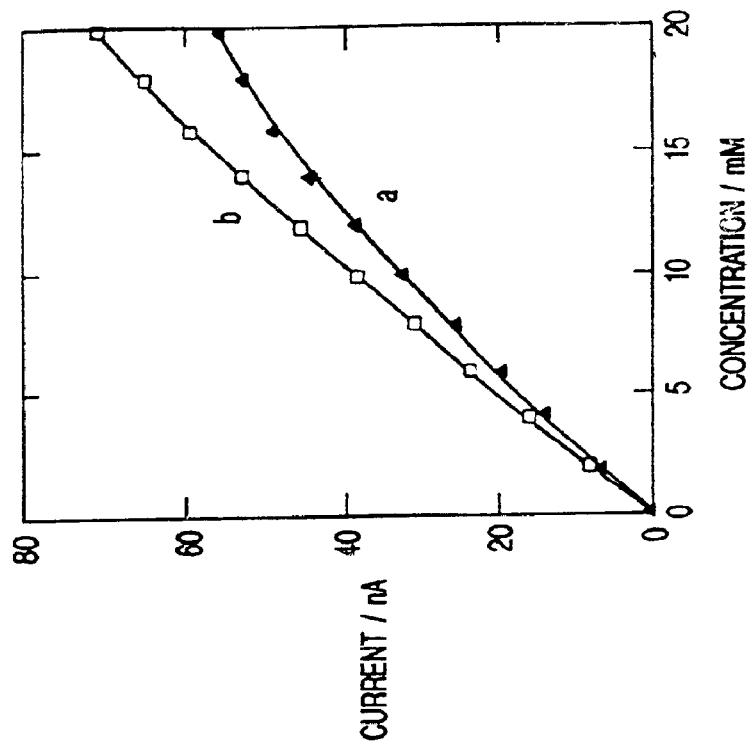
FIG. 9 is a graph showing calibrations of glucose on the GOx-modified mineral oil carbon paste electrode without (A) and with (B) 10% myoglobin in the absence (a) and presence (b) of oxygen.
Figure 9A:
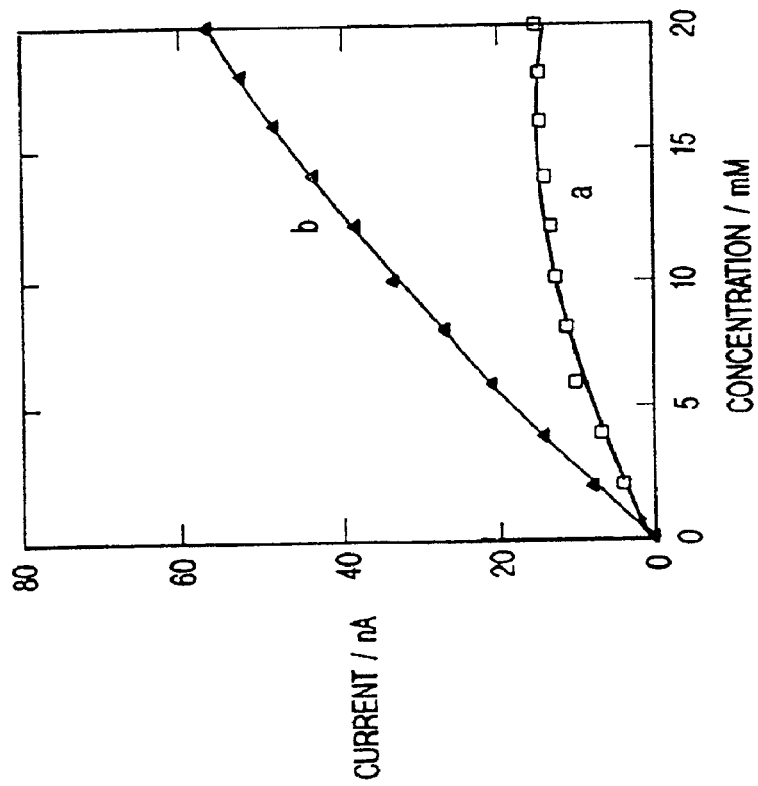

FIG. 9 illustrates the responses of a composite bioelectrode without fluorocarbons, using myoglobin as the oxygen source and additive. As indicated, the addition of myoglobin (b) in the carbon paste greatly improved the current reading of glucose in the absence of oxygen to that of the reading in the presence of oxygen, thus minimizing the oxygen dependence.

EXAMPLE 10

Figure 10:
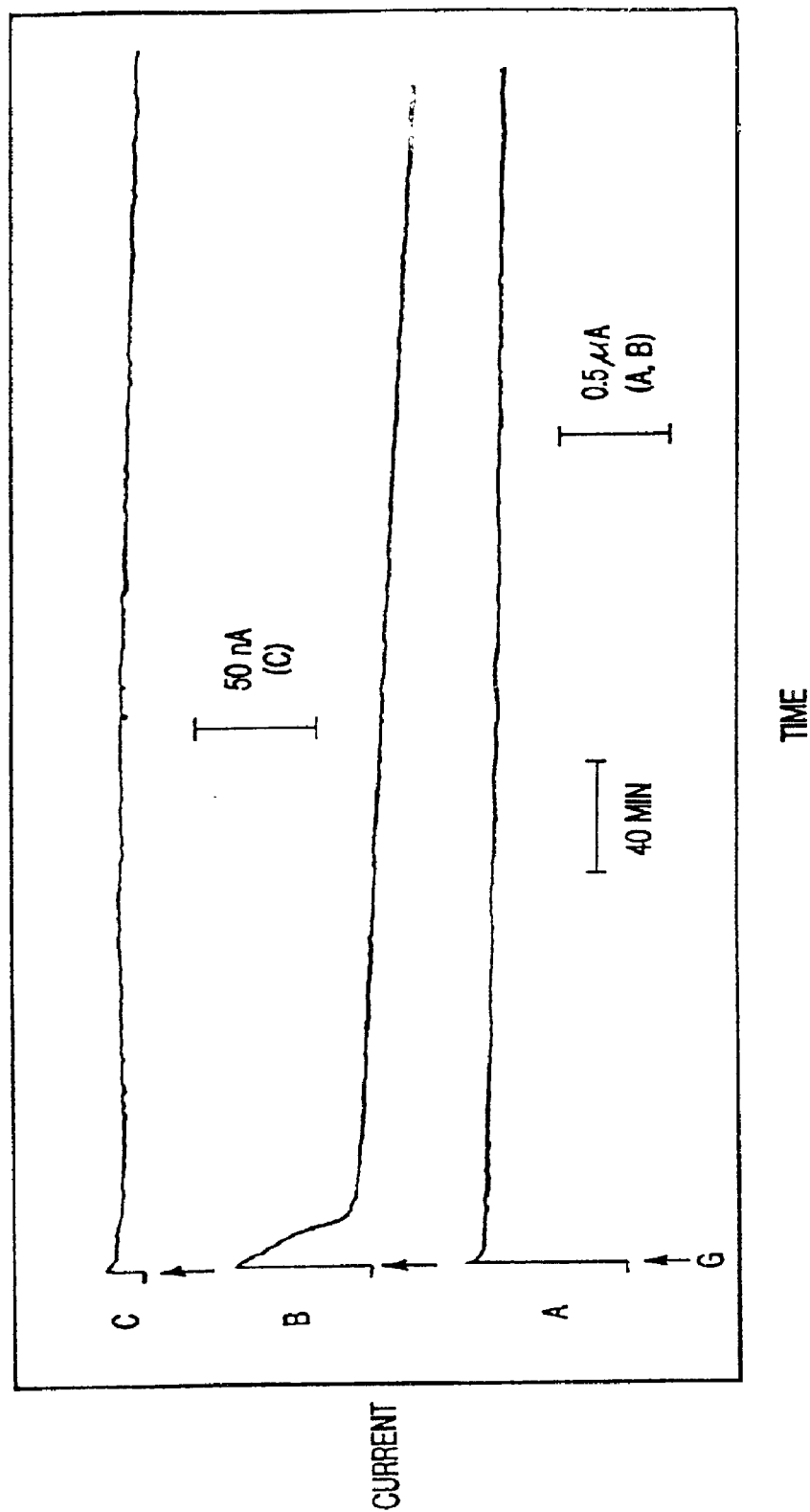
FIG. 10 is a graph showing the amperometric response to the addition of glucose to a deoxygenated buffer solution at Kel-F/GOx/CPEs (A,C) and mineral oil/GOx/CPE (B)

A key issue for addressing the oxygen demand of oxidase biosensors is the ability of the internal oxygen reservoir to reliably deliver oxygen over an extended period of time. FIG. 10 illustrates such capability in connection with measurements of 5 mM glucose in a deoxygenated solution over a prolonged, 7 hour continuous operation. Electrode diameter in A and B was 3 mm, and in C was 0.25 mm. The stable response (A) indicated no apparent depletion of oxygen from the internal fluorocarbon reservoir. In contrast, the mineral oil carbon paste biosensor (with its limited oxygen capacity) displayed a rapid, nearly complete loss of the glucose response within the first 20 minutes of operation in the deoxygenated medium (B). Smaller Kel-F/carbon paste biosensors, relevant to in vivo glucose monitoring, were also tested (C). The 0.2 mm o.d. enzyme microelectrode displayed a nearly constant glucose output in the absence of solution oxygen throughout this 7 hour operation, with the exception of a 15% initial loss. The lower biocatalytic consumption of oxygen, related to the smaller electrode surface area, thus compensates for its smaller oxygen reservoir. Hence, a prolonged operation of the microelectrode in deoxygenated medium did not deplete its internal oxygen supply. A further size reduction is compensated by employing long carbon-paste reservoirs containing available oxygen. The enzyme microelectrode also displayed a linear, oxygen-independent response over the 2–25 mM clinically relevant glucose concentration range.

EXAMPLE 11

The confinement of GOx within fluorinated CPEs had no detrimental effect upon the enzyme activity. A nearly identical glucose response was obtained using the same Kel-F CPE surface (3 mm diameter) over a 75 day period, with intermittent storage at 4° C. Such Kel-F confinement resulted also in a remarkable thermal stability, as was indicated from the identical glucose response before and after a 24 hour stress at 90° C.

EXAMPLE 12

Figure 11:
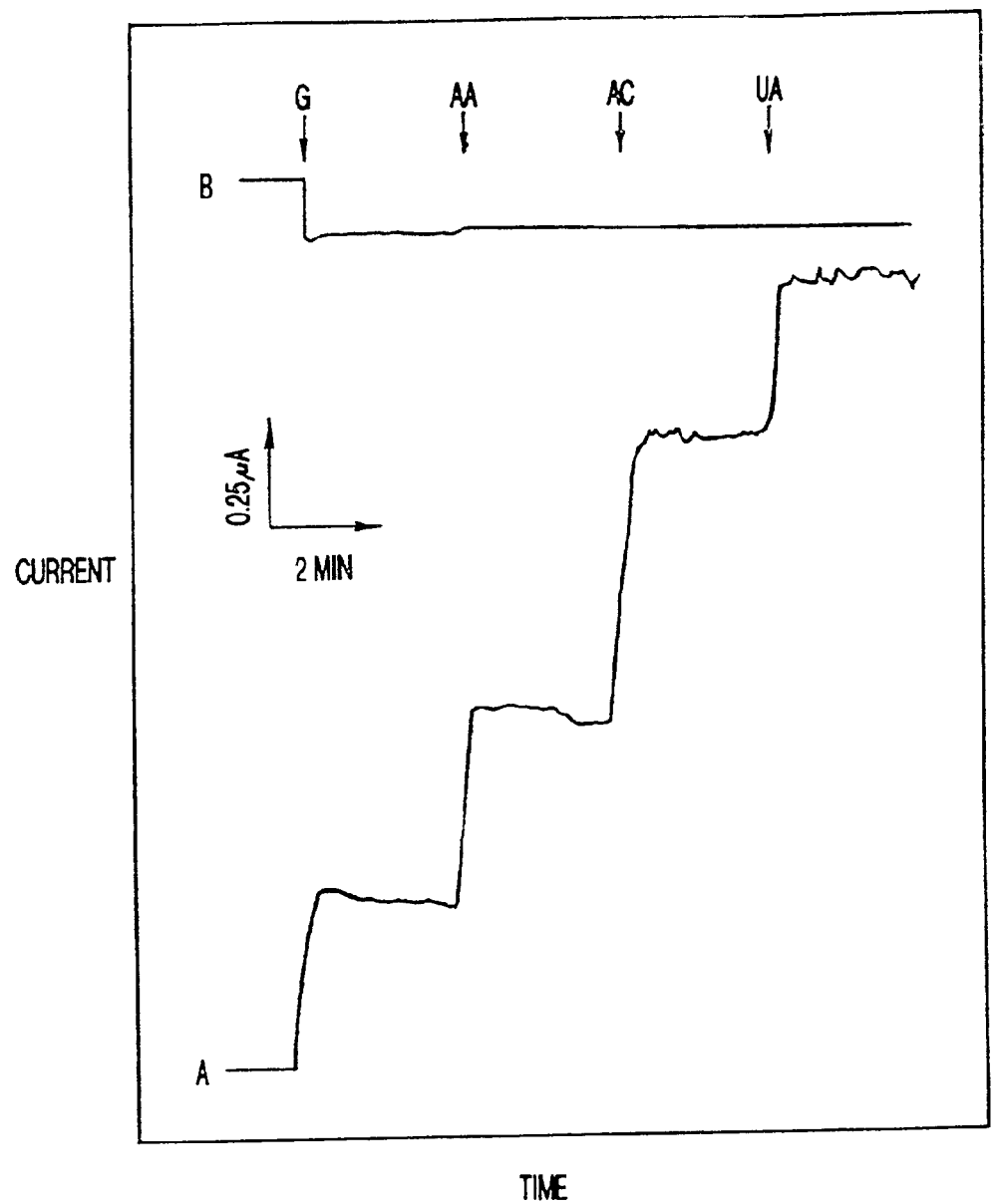
FIG. 11 is a graph of current-time recordings for a deoxygenating buffer solution upon addition of glucose (G), ascorbic acid (AA), acetaminophen (AC), and uric acid (UA).

As illustrated in FIG. 11, the glucose response (in the absence of oxygen) was not influenced by the presence of ascorbic acid, acetaminophen or uric acid. The electric current in A was +0.6 V, and in B was −0.05 V. At higher potentials, all three oxidizable compounds displayed a significant response, and the selectivity is compromised.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for producing a signal related to the concentrations of glucose and insulin, said apparatus comprising:
    a first conductive composite comprising a glucose oxidase and a metal posited within a first cylindrical tube;
    a second conductive composite comprising a $RuO_x$ or $IrO_x$ catalyst posited within a second cylindrical tube;
    a sleeve containing the first cylindrical tube and the second cylindrical tube;
    a first electrical contact within the first cylindrical tube in contact with the first conductive composite; and
    a second electrical contact within the second cylindrical tube in contact with the second conductive composite.

2. The apparatus of claim 1 wherein the first conductive composite comprises a carbon powder conductor.

3. The apparatus of claim 1 wherein the sleeve comprises a conductor.

4. The apparatus of claim 3, further comprising an insulating layer posited on the exterior the sleeve and a conducting layer posited on the insulating layer.

5. The apparatus of claim 1 wherein the first cylindrical tube and the second cylindrical tube comprise an interior diameter of less than 500 µm.

6. The apparatus of claim 1 wherein the first conductive composite comprises an oxygen-rich binder.

7. The apparatus of claim 6 wherein the oxygen-rich binder comprises at least one compound selected from the group consisting of perfluorochemical, myoglobin, and hemoglobin.

8. The apparatus of claim 7 wherein the perfluorochemical comprises polychlorotrifluoroethylene.

9. An apparatus for producing a signal related to the concentration of a substance, said apparatus comprising:
    a first conductive composite comprising an oxygen-dependent enzyme and sufficient oxygen-rich binder to support an oxygen-dependent enzymatic reaction in the absence of exogenous oxygen, a second conductive composite comprising a $RuO_x$ or $IrO_x$ catalyst;

a sleeve with a first end and second end;

a first cavity disposed within the first end of said sleeve wherein the length of the sleeve is at least about 0.2 mm, said cavity containing said first composite and forming an electrode end of said composite at the first end of said sleeve;

a second cavity containing said second composite; and an electrical contact disposed within the second end of said sleeve extending into said cavity;

wherein the ratio of the surface area of the electrode end of said composite to the volume of said composite is at least about 1:8.

10. The apparatus of claim 9 wherein said first conductive composite comprises a metal powder conductor.

11. The apparatus of claim 9 wherein said first conductive composite comprises a carbon powder conductor.

12. The apparatus of claim 11 wherein said carbon powder comprises a metalized graphite.

13. The apparatus of claim 12 wherein said metalized graphite comprises at least one metal selected from the group consisting of rhodium, iridium, and ruthenium.

14. The apparatus of claim 9 wherein the sleeve comprises an insulator.

15. The apparatus of claim 14 wherein said insulator comprises polytetrafluoroethylene.

16. The apparatus of claim 9 wherein said cavity comprises a diameter of between approximately 0.2 mm and approximately 5.0 mm.

17. The apparatus of claim 16 wherein said first cavity comprises a diameter of 2.0 mm.

18. The apparatus of claim 9 wherein said oxygen-rich binder comprises at least one compound selected from the group consisting of perfluorochemical, myoglobin, and hemoglobin.

19. The apparatus of claim 18 wherein said perfluorochemical comprises polychlorotrifluoroethylene.

20. The apparatus of claim 9 wherein said oxygen-dependent enzyme comprises an oxidase enzyme.

21. The apparatus of claim 9 wherein said oxygen-dependent enzyme comprises glucose oxidase.

22. The apparatus of claim 9 further comprising a protective membrane covering at least a portion of the electrode end of the first conductive composite.

23. The apparatus of claim 22 wherein said membrane comprises at least one compound selected from the group consisting of polyurethane, polycarbonate, polyethylene glycol, polyvinyl chloride and polyhydroethylmethacrylate.

24. The apparatus of claim 22 wherein said membrane comprises an oxygen-rich film.

25. The apparatus of claim 24 wherein said film comprises at least one compound selected from the group consisting of Pluronic F-68 and a perfluorosulfonate isomer.

26. The apparatus of claim 9 wherein said sleeve comprises a needle.

27. A method of simultaneous detection of glucose and insulin in a liquid sample, the method comprising the following steps:

a) providing a first screen-printed, thick-film biosensor comprising glucose oxidase;

b) providing a second screen-printed, thick-film biosensor comprising a metal oxide catalyst;

c) simultaneously placing the first biosensor and the second biosensor in the liquid sample;

d) applying a detection potential to the first biosensor and the second biosensor;

e) detecting a biocatalytic signal at the first biosensor; and f) detecting an electrocatalytic signal at the second biosensor wherein providing a first screen-printed, thick-film biosensor comprising glucose and providing a second screen-printed, thick-film biosensor comprising a metal oxide catalyst comprises providing a dual sensor test strip with the first screen-printed, thick-film biosensor and second screen-printed, thick-film biosensor disposed thereon.

28. The method of claim 27 wherein detecting comprises amperometric detection.

29. The method of claim 27 wherein detecting comprises stripping potentiometry.

30. The method of claim 27 wherein the metal oxide catalyst comprises at least one member selected from the group consisting of $RuO_x$ and $IrO_x$.

31. The method of claim 27, wherein the first biosensor comprises an oxygen-rich binder.

32. A method of detecting substrate concentration of an environment using a composite biosensor, the method comprising the following steps:

a) providing a biosensor comprising (1) a first conductive composite comprising sufficient oxygen-rich binder to support an oxygen-dependent enzymatic reaction in the absence of exogenous oxygen, a conductor, an oxygen-dependent enzyme, a first reservoir containing the first composite, and an electrode end of the first composite, wherein the ratio of the surface area of the electrode end of said first composite to the volume of said first composite is at least about 1:8, and (2) a second reservoir containing a second conductive composite comprising a metal oxide selected from the group consisting of $RuO_x$ and $IrO_x$, b) placing the biosensor in the environment, and c) detecting the substrate concentration.

33. The method of claim 32 wherein the step of providing a biosensor comprises providing a biosensor comprising a metal powder conductor.

34. The method of claim 32 wherein the step of providing a biosensor comprises providing a biosensor comprising a carbon powder conductor.

35. The method of claim 34 wherein the step of providing a biosensor comprises providing a biosensor comprising a metalized graphite.

36. The method of claim 35 wherein the step of providing a biosensor comprises providing a biosensor comprising at least one metal selected from the group consisting of rhodium, iridium, and ruthenium.

37. The method of claim 32 wherein the step of providing a biosensor comprises providing a biosensor comprising at least one oxygen-rich binder compound selected from the group consisting of perfluorochemical, myoglobin, and hemoglobin.

38. The method of claim 32 wherein the step of providing a biosensor comprises providing a biosensor comprising a cylindrical reservoir with a diameter of between approximately 0.2 mm and approximately 5.0 mm.

39. The method of claim 32 wherein the step of providing a biosensor comprises providing a biosensor comprising an oxidase enzyme.

40. The method of claim 32 wherein the step of providing a biosensor further comprises providing a biosensor comprising a sleeve.

41. The method of claim 32 wherein the step of placing the biosensor in the environment comprises placing the biosensor in an in vivo environment.

42. The method of claim 32 wherein the step of placing the biosensor in the environment comprises placing the biosensor in an ex vivo clinical environment.

43. The method of claim 32 wherein the step of placing the biosensor in the environment comprises placing the biosensor in an industrial environment.

44. The method of claim 32 wherein the step of detecting the substrate concentration comprises detecting an inhibitor concentration.

45. The method of claim 32 wherein the step of detecting the substrate concentration comprises detecting the substrate concentration comprising approximately 1.0 $\mu$molar–0.2 molar concentration.

46. The method of claim 32 wherein the step of detecting the substrate concentration comprises detecting at least one substance selected from the group consisting of glucose, lactate, and cholesterol.

* * * * *